(12) United States Patent
Mizuyoshi

(10) Patent No.: US 8,251,897 B2
(45) Date of Patent: Aug. 28, 2012

(54) ENDOSCOPE LIGHT SOURCE DEVICE

(75) Inventor: Akira Mizuyoshi, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 582 days.

(21) Appl. No.: 12/369,394

(22) Filed: Feb. 11, 2009

(65) Prior Publication Data

US 2009/0203966 A1    Aug. 13, 2009

(30) Foreign Application Priority Data

Feb. 13, 2008    (JP) ................................. 2008-031485

(51) Int. Cl.
*A61B 1/06* (2006.01)

(52) U.S. Cl. .......................... 600/182; 600/178; 600/180

(58) Field of Classification Search .......... 600/178–182; 362/553, 555, 574
See application file for complete search history.

(56) References Cited

U.S. PATENT DOCUMENTS

| | | | |
|---|---|---|---|
| 5,058,978 A * | 10/1991 | Kondoh et al. | 385/43 |
| 5,377,287 A * | 12/1994 | Lee et al. | 385/35 |
| 5,751,869 A * | 5/1998 | Li et al. | 385/33 |
| 6,219,480 B1 | 4/2001 | Cassarly et al. | 385/46 |
| 6,485,414 B1 * | 11/2002 | Neuberger | 600/182 |
| 6,570,897 B1 * | 5/2003 | Mizuyoshi | 372/43.01 |
| 6,692,431 B2 * | 2/2004 | Kazakevich | 600/178 |
| 6,936,004 B2 * | 8/2005 | Utsui | 600/182 |
| 7,329,887 B2 * | 2/2008 | Henson et al. | 250/494.1 |
| 2006/0235277 A1* | 10/2006 | Ohkubo et al. | 600/179 |
| 2006/0287582 A1 | 12/2006 | Toda | |
| 2006/0293562 A1* | 12/2006 | Uchimura et al. | 600/110 |
| 2007/0106120 A1* | 5/2007 | Iijima | 600/182 |
| 2007/0213592 A1* | 9/2007 | Yamada | 600/178 |
| 2008/0089089 A1* | 4/2008 | Hama et al. | 362/574 |
| 2008/0262316 A1* | 10/2008 | Ajima et al. | 600/178 |
| 2009/0167149 A1* | 7/2009 | Ito | 313/501 |

FOREIGN PATENT DOCUMENTS

| | | |
|---|---|---|
| EP | 1 795 798 A1 | 6/2007 |
| JP | 04-310027 A | 11/1992 |
| JP | 07-246186 A | 9/1995 |
| JP | 2006-166983 A | 6/2006 |
| JP | 2007-020939 A | 2/2007 |
| WO | 01/97902 A2 | 12/2001 |
| WO | 01/97902 A3 | 12/2001 |

OTHER PUBLICATIONS

EP Communication, dated May 18, 2009, issued in corresponding EP Application No. 09001976.1, 6 pages.
Notification of Reasons for Refusal, dispatched Jun. 26, 2012, issued in corresponding JP Application No. 2008-031485, 3 pages with partial English translation.

* cited by examiner

*Primary Examiner* — Philip R Smith
*Assistant Examiner* — William Chou
(74) *Attorney, Agent, or Firm* — Sughrue Mion, PLLC

(57) ABSTRACT

The endoscope light source device includes a semiconductor light source, optical fibers that are inserted into an endoscope, guide first light beams from the semiconductor light source, and are arranged in plural rows in at least an angle portion of the endoscope, an optical coupling circuit that is arranged at a distal end side of the endoscope with respect to the angle portion, and couples the first light beams guided by the optical fibers arranged in the plural rows to obtain a coupled light beam and a wavelength conversion part that is arranged at a distal end side of an endoscope insertion section in the optical coupling circuit, and converts a part or all of the coupled light beam from the optical coupling circuit into a converted light beam having a given wavelength by a phosphor.

10 Claims, 4 Drawing Sheets

ENDOSCOPE LIGHT SOURCE DEVICE

BACKGROUND OF THE INVENTION

The present invention relates to an endoscope light source device.

An endoscope has an insertion section, which is inserted into the living body such as the human body, and is used for diagnosis or treatment of organs, collection of specimens, and so forth. The distal end of the insertion section of the endoscope is provided with an imaging element for acquiring an image, and an output window for an illumination light for illuminating an observed region. A light guide formed of a bundle of optical fibers is inserted into the endoscope, and is connected to a white light source such as a xenon lamp to transmit a light from the light source to the distal end of the insertion section.

As an endoscopic illumination method, a method is known in which the light beams emitted from two points at the distal end of an endoscope are used to illuminate a subject, while taking a shadow caused by the illumination light and a light distribution characteristic into consideration. In this case, the light guide is branched into a plurality of guides inside the endoscope to transmit the light beam obtained from one light source as a plurality of light beams inside the endoscope. However, when the light guide is branched inside the endoscope, there arises a problem in that buckling or disconnection is likely to occur in the branch portion of the light guide upon bending of the endoscope. In order to address the problem, JP 07-246186 A has proposed to dispose the branch portion of the light guide closer to the subject than the bending portion of the endoscope.

On the other hand, it has been proposed to employ as a light source a laser light source to cope with the rise in temperature in the surroundings of the light source due to the heat generated by the light source lamp such as a xenon lamp, or the attenuation of light. Further, JP 2006-166983 A has proposed that a plurality of laser light sources are prepared and sequentially changed over upon use for the purpose of performing a high-precision temperature management of the laser light sources. In the endoscope device disclosed in JP 2006-166983 A, a light guide extends from each of the laser light sources, and the light guides are integrated into one guide before the endoscope device, and inserted into the endoscope device. It is stated in JP 2006-166983 A that the endoscope device disclosed in the document sequentially changes over a plurality of laser light sources upon use, thereby enabling the durability of the laser light sources to be enhanced by suppressing the rise in temperature around the laser light sources, and enabling a clear observation image to be obtained even if the endoscope device is used for a long period of time.

FIG. 7 schematically illustrates such an example of the conventional endoscope device as illustrated in JP 2006-166983 A. Referring to FIG. 7, an endoscope system 100 includes an endoscope device 102 and a control device 104, and the control device 104 is provided with a processor 130 and a plurality of laser light sources LD1 and LD2. The endoscope device 102 comprises an insertion section 106, an operation section 108, a universal cord section 110, and a connector section 112. The insertion section 106 includes a soft portion 114 with flexibility, a bending portion 116, and a distal end portion 118. The distal end portion 118 of the insertion section 106 is provided with a phosphor 120, an illumination window 122 for an illumination light, an objective lens (not shown), and a CCD 124.

A light guide 126, which is formed of the light guides connected to the laser light sources LD1 and LD2, respectively, and integrated into one guide before the endoscope device 102, is inserted into the endoscope device 102. The distal end of the light guide 126 reaches the position of the phosphor 120, and inputs the light beams from the laser light sources LD1 and LD2 to the phosphor 120.

The CCD 124 is connected to the processor 130 of the control device 104 by means of a cable (scope cable) 128 for transmitting an imaging signal. The processor 130 converts the imaging signal that has been transmitted from the CCD 124 into a video signal, and then supplies the video signal to a monitor or the like.

However, in the conventional light guide, a large number of, such as one thousand, optical fibers are bundled into the light guide, and hence some of the optical fibers are damaged even in a portion other than the branched portion discussed as a problem in JP 07-246186 A, due to frictions among the optical fibers or difference in tension between the inner curve and the outer curve of a bent fiber in the bending portion or the like, thereby reducing the number of effective optical fibers in use for a long period of time. For that reason, the optical output from the illumination portion is gradually deteriorated. Further, the endoscope using the conventional light guide has problems in that it is very difficult to reduce the diameter of the insertion section, and the minimum bending radius is large.

Further, in the case of a semiconductor laser beam, an optical fiber with a single core is higher in coupling efficiency between a laser beam and an optical fiber than the conventional bundle fiber used for guiding light such as light from a xenon lamp, and can efficiently guide light up to the distal end portion.

Under the above-mentioned circumstances, it is conceivable to independently use the optical fiber with a single core instead of the bundle fiber as a light guide path. The use of the optical fiber with a single core can reduce damage on the optical fibers repetitively used, which is caused by the frictions among the optical fibers, and substantially increase the strength of the optical fibers. Further, it is possible to decrease the diameter of the endoscope insertion section, and reduce the bending radius.

However, even the optical fiber with a single core cannot completely eliminate the risk of its deterioration, buckling, or breaking, which is caused by sliding inside the endoscope when the endoscope is bent. In addition, the optical fiber may be damaged if a big impact or an external factor (such as dust contamination) should occur. In the case of using only one optical fiber with a single core, if the optical fiber is damaged, the optical output becomes zero, and illumination stops.

For example, in the conventional endoscope system 100 illustrated in FIG. 7, when it is assumed that the light guide 126 is replaced with the optical fiber with a single core, even if one of the laser light sources LD1 and LD2 stops light emission, the other laser light source is switchingly used, thereby enabling the illumination light to be ensured. However, when the optical fiber is disconnected, the illumination light from the distal end of the endoscope device 102 completely stops so that the field of view becomes pitch-dark. If illumination stops while the endoscope is inserted into the body, the image of the surroundings cannot be checked when the endoscope is drawn out of the body, resulting in the fear that it is difficult to keep sufficient safety.

SUMMARY OF THE INVENTION

The present invention has been made to solve the above-mentioned problems with the related art, and therefore an object of the present invention is to provide an endoscope light source device, which reduces the problems of a damage on an optical fiber and a deterioration of an optical output with time, which is caused by the damaged optical fiber, in the conventional endoscope device using a conventional light guide formed of a bundle of optical fibers, enables reductions in a diameter of an endoscope insertion section and a minimum bending radius to be realized, and can ensure safe use of the endoscope without stopping illumination even when the optical fiber is damaged.

In order to achieve the object as above, the present invention provides an endoscope light source device comprising: at least one semiconductor light source; optical fibers that are inserted into an endoscope, guide first light beams from the at least one semiconductor light source, and are arranged in plural rows in at least an angle portion of the endoscope; an optical coupling circuit that is arranged at a distal end side of said endoscope with respect to the angle portion, and couples the first light beams guided by the optical fibers arranged in the plural rows to obtain a coupled light beam; and at least one wavelength conversion part that is arranged at a distal end side of an endoscope insertion section in the optical coupling circuit, and converts a part or all of the coupled light beam from the optical coupling circuit into a converted light beam having a given wavelength by a phosphor.

It is preferable that the endoscope light source device further comprises an optical branching circuit that is disposed at the distal end side of the endoscope insertion section in the optical coupling circuit, and branches the coupled light beam from the optical coupling circuit into second light beams, and the at least one wavelength conversion part includes plural wavelength conversion parts that are provided corresponding to the second light beams branched by the optical branching circuit.

Preferably, the optical coupling circuit and the optical branching circuit are integrated with each other.

It is also preferable that the at least one semiconductor light source includes plural semiconductor light sources that are provided, and the optical fibers arranged in the plural rows are respectively connected to the plural semiconductor light sources different each other.

Alternatively, the at least one semiconductor light source may include one semiconductor light source that is disposed. In that case, it is preferable that a light source side optical branching circuit that divides a light beam from the one semiconductor light source into plural light beams is disposed between the one semiconductor light source and the endoscope, or disposed on a proximal end side with respect to the angle portion within the endoscope.

It is also preferable that the at least one semiconductor light source includes one semiconductor light source that is disposed, and the optical fibers arranged in the plural rows are connected to the one semiconductor light source.

According to the present invention, the light beam emitted from a single semiconductor light source or plural semiconductor light sources is guided by a plurality of independent optical fibers in at least the angle portion of the endoscope, and the optical fibers are coupled together on the distal end side with respect to the angle portion (bending portion) of the endoscope insertion section, with the light beams from the light source or sources being coupled together and emitted to the illumination portion. With the above-mentioned configuration, even when one of the optical fibers is disconnected halfway, safe use of the endoscope can be ensured without stopping the illumination light.

Further, according to an embodiment of the present invention, the light beam emitted from a single semiconductor light source or a plurality of semiconductor light sources is guided by a plurality of independent optical fibers in at least the angle portion of the endoscope, and the optical fibers are coupled together, then branched again, on the distal end side with respect to the angle portion of the endoscope insertion section, with the light beams from the light source or sources being coupled together, then branched again, accordingly. With the above-mentioned configuration, even if one of the optical fibers is disconnected halfway, it is possible to ensure a usual light emission from a plurality of points. As a result, the safe use of the endoscope can be ensured, and in addition, an image with a sufficient quality can be obtained.

DETAILED DESCRIPTION OF THE PREFERRED EMBODIMENTS

A description is given in detail of an endoscope lighting device according to preferred embodiments of the present invention with reference to the accompanying drawings.

First, a first embodiment of the present invention is described.

Figure 1:
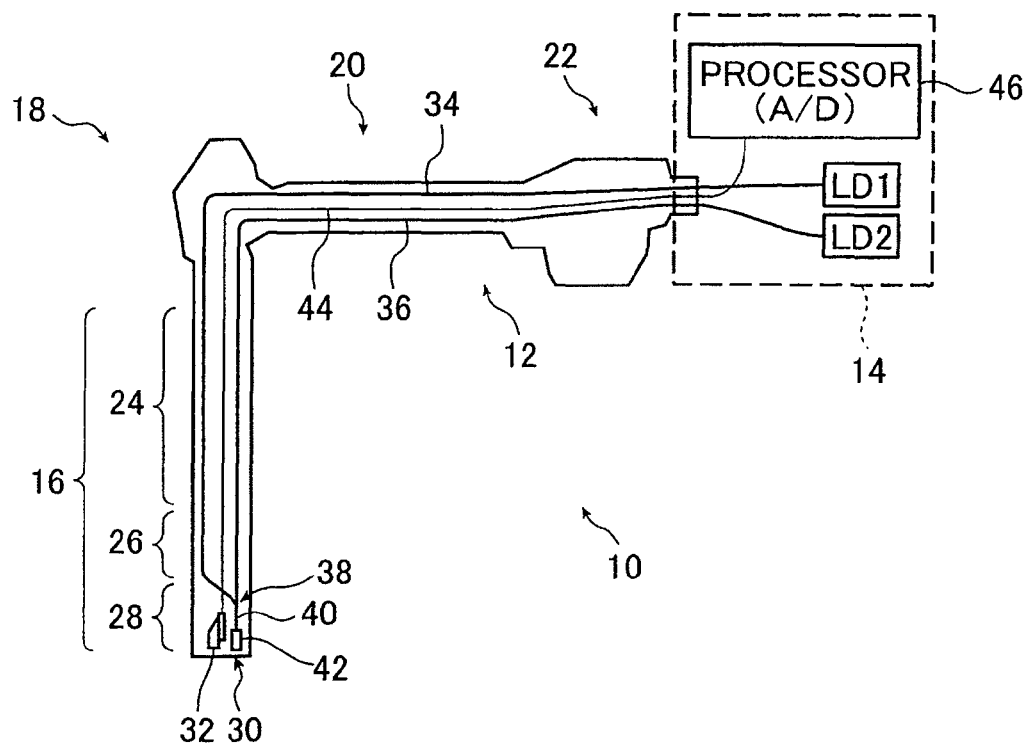
FIG. 1 is a schematic cross-sectional diagram illustrating a first embodiment of the present invention.

FIG. 1 is a schematic diagram illustrating a first example of an endoscope system using an endoscope lighting device according to the present invention. An endoscope system 10 illustrated in FIG. 1 includes an endoscope 12 and a control device 14. In FIG. 1, the endoscope 12 is illustrated with a schematic cross-sectional diagram, and an image optical system arrangement and an optical path inside the endoscope 12 are illustrated.

The endoscope 12 is a so-called electronic endoscope that has a compact television camera (CCD) at a distal end thereof, and transmits acquired image information to the control device 14 as an electric signal.

The control device 14 includes two semiconductor laser light sources (semiconductor light emitting elements) LD1 and LD2, and a processor 46. The processor 46 converts an electric signal (imaging signal) that has been transmitted from the endoscope 12 into a digital image signal (video signal), subjects the digital image signal to image processing, and supplies the processed signal to an image output device such as a television monitor.

The endoscope 12 includes an insertion section 16 configured to be inserted into the body, an operation section 18 for conducting the angle operation of a distal end of the insertion section 16 and such operations as suction, air supply, or water supply from the distal end of the insertion section 16, a connector section 22 that connects the endoscope 12 to the control device 14, and a universal cord section 20 that joins the operation section 18 and the connector section 22.

For facilitation of understanding the configuration, the dimension ratio of the endoscope 12 of FIG. 1 is different from a real dimension ratio. For example, the insertion section 16 is actually remarkably thinner than other parts, and has a length sufficient to reach a region to be observed. Further, though being not illustrated, a forceps channel into which a tissue collection treatment tool is inserted, air supply and water supply channels, and the like are disposed inside the endoscope 12 in addition to the image optical system.

The insertion section 16 includes a soft portion 24 with flexibility, an angle portion 26, and a distal end portion 28. The distal end portion 28 is provided with an illumination window 30 for illuminating an observed region with light, an imaging element (CCD) 32 for acquiring image information on the observed region, and an objective lens (not shown).

The angle portion 26 is disposed between the soft portion 24 and the distal end portion 28, and configured to be bendable by the wire operation or actuator operation from the operation section 18. The angle portion 26 can be bent at an arbitrary angle determined according to a region for which the endoscope 12 is used, for example, at angles of 0 to 210 degrees upward, 0 to 90 degrees downward, and 0 to 100 degrees laterally. The angle portion 26 is so bent as to direct the illumination window 30 and the imaging element 32 of the distal end portion 28 to the region to be observed. The minimum bending radius of the angle portion 26 is set to, for example, 7.5 mm.

Two optical fibers 34 and 36, and one scope cable 44 extend in the inside of the endoscope 12 along its entire length.

The optical fibers 34 and 36 have their proximal ends connected to the semiconductor laser light sources LD1 and LD2, respectively, with connection of the connector section 22 on the near side (proximal end side) of the endoscope 12 with the control device 14, thereby guiding laser beams from the semiconductor laser light sources LD1 and LD2 toward the distal end of the endoscope 12. The optical fibers 34 and 36 are arranged in parallel to each other, independently, while they extend from the connector section 22 over the angle portion 26 of the insertion section 16 through the universal cord section 20, and are then coupled together by an optical coupling circuit 38 after passing through the angle portion 26 to provide one optical fiber 40.

The scope cable 44 has a distal end connected to the imaging element 32, and the connector section 22 of the endoscope 12 is connected to the control device 14 with the result that the proximal end of the scope cable 44 is connected to the processor 46. The image information acquired by the imaging element 32 is transmitted to the processor 46 through the scope cable 44.

Figure 2:
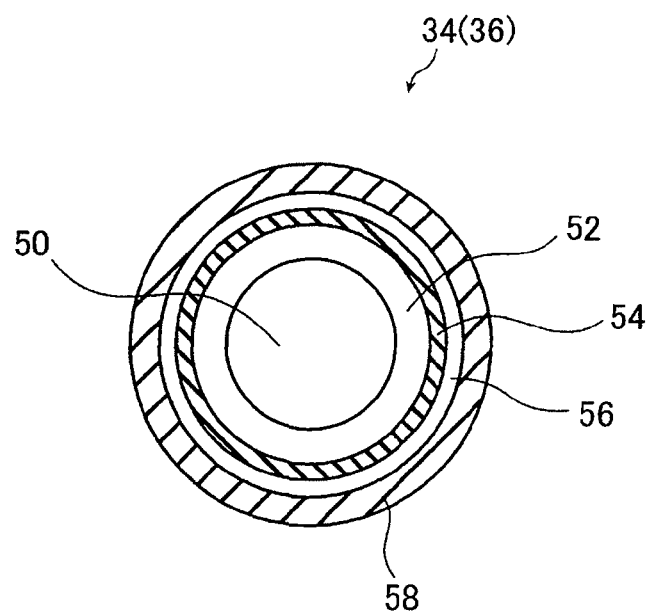
FIG. 2 is a schematic cross-sectional diagram illustrating an example of an optical fiber.

The optical fibers 34 and 36 have the same configuration with a single core. FIG. 2 illustrates a cross-sectional configuration of an example of the optical fiber 34. The optical fiber 34 has a core 50, a cladding 52, a hard cladding 54, a reinforcing member 56 made of polyimide, and a Teflon coating 58 in the stated order from the central portion. For example, when it is assumed that the core 50 is 200 µm in diameter, the cladding 52 is 35 µm in thickness, the hard cladding 54 is about 5 µm, the reinforcing member 56 made of polyimide is 5 to 10 µm, and the Teflon coating 58 is about 100 µm, the diameter of the optical fiber 34 is about 0.3 to 0.5 mm. This corresponds to the half or less of the diameter of the conventional light guide.

The optical fiber with a single core is used for each of the optical fibers 34 and 36, thereby making it possible to substantially increase the strength without occurrence of a friction between the optical fibers as with the conventional light guide using the bundle of optical fibers. Further, the optical fibers 34 and 36 can prevent such a problem as the deterioration of an optical output with time which is caused by damage on the optical fibers repetitively used. Further, it is possible to greatly promote the reduction of the diameter of the endoscope insertion section, and reduce the bending radius.

The optical coupling circuit 38 is disposed in the distal end portion 28 located on the distal end side with respect to the angle portion 26, and couples the light beams from the semiconductor laser light sources LD1 and LD2 which have been transmitted through the optical fibers 34 and 36. For example, a Y-branching circuit as illustrated in FIG. 1 can be used for the optical coupling circuit 38. The Y-branching circuit is preferable because the number of components is small, and the configuration is simple. Apart from the Y-branching circuit, a directional coupler that makes two optical waveguides closer to each other can be employed for the optical coupling circuit 38. Alternatively, a bulk type optical circuit using a prism or a fiber type optical circuit can be used. The use of the optical fibers 34 and 36 each having a single core can allow the optical fibers 34 and 36 to be coupled together by the optical coupling circuit 38 with a simple configuration.

The features of the present invention reside in that the optical fibers each having a single core are used for the optical fibers 34 and 36, and that the optical fibers 34 and 36 are coupled together by the optical coupling circuit 38.

That is, up to now, the light guide used as the optical waveguide is of a bundle type in which a large number of optical fibers are bundled, and hence it is not easy to couple two light guides into one light guide, the configuration is complicated, and the loss is large. With the above-mentioned problems, it is difficult to efficiently perform optical coupling. For that reason, it is very difficult to perform optical coupling in a limited length of the distal end portion 28 of the endoscope 12. The difficulty is greater as the light guide is thicker to transmit a larger quantity of light.

On the contrary, in the present invention, the optical fiber with a single core is used for each of the optical fibers 34 and 36 as in the endoscope system 10 illustrated in FIG. 1, and hence a plurality of optical fibers can be efficiently coupled together with a relatively simple configuration such as the Y-branching circuit. The above-mentioned configuration makes it possible that two optical fibers 34 and 36 are coupled together to couple the light beams in the distal end portion 28 located on the distal end side with respect to the angle portion 26 of the endoscope 12.

The light beams that have been guided by the optical fibers 34 and 36 are coupled together by the optical coupling circuit 38, and thereafter guided to a phosphor converter 42. The semiconductor laser light sources LD1 and LD2, the optical fibers 34 and 36, the optical coupling circuit 38, and the phosphor converter 42 constitute the endoscope light source device of the present invention.

The phosphor converter 42 is disposed in the vicinity of the illumination window 30 in the distal end portion 28 of the insertion section 16. The phosphor converter 42 includes a phosphor. The light beam that has been coupled by the optical coupling circuit 38 is transmitted to the phosphor converter 42 by the optical fiber 40 to excite the phosphor of the phosphor converter 42. The phosphor converter 42 converts a part of excitation light beam into a fluorescent light beam different in wavelength from the excitation light beam to output the fluorescent light beam, and also allows the remaining excitation light beam to pass therethrough. The fluorescent light beam and the excitation light beam which are output from the phosphor converter 42 are combined together to provide, for example, a white illumination light beam. The illumination light beam is emitted from the illumination window 30, and the observed region is thus illuminated with it.

For example, a light source of a blue light beam that is 445 nm in wavelength is used for each of the semiconductor laser light sources LD1 and LD2, a phosphor of YAG system, or α-sialon and $CaSiSiN_3$ that emits a light beam in a red region are used for the phosphor converter 42, and the phosphor converter 42 is excited with the light beams from the semiconductor laser light sources LD1 and LD2 as the excitation light beam. Then, the fluorescent light beam ranging in color from red to green which has been converted by the phosphor converter 42, and the blue excitation light beam which has passed through the phosphor converter 42 are emitted from the phosphor converter 42. Those two light beams are combined together, thereby making it possible to obtain white light emission from the illumination window 30.

In the endoscope system 10 with the endoscope light source device according to the present invention, the two optical fibers 34 and 36 are arranged in parallel, independently, until they pass through the angle portion 26 of the endoscope 12, which is a portion having a small bending radius and being frequently bent, and the optical fibers 34 and 36 are coupled together after having passed through the angle portion 26. The two optical fibers 34 and 36 are arranged at the angle portion 26 where a load is most likely to be exerted on the optical fibers, and hence, even if one of the optical fibers 34 and 36 is damaged or disconnected halfway, illumination light does not become zero (illumination is not stopped) and the field of view does not become pitch-dark though the light quantity is reduced in half. As a result, the image of the surroundings can be checked when the endoscope 12 is drawn out, whereby the operation safety of the endoscope 12 can be ensured.

Further, when the semiconductor lasers are used as the light sources, there is a mode called "fast degradation" as a mode of the element degradation, in which it is known that the optical output is suddenly remarkably degraded. However, the endoscope system 10 is connected to the two semiconductor laser light sources LD1 and LD2, and hence, even if one laser light source is suddenly degraded, illumination light does not become zero though the light quantity is reduced in half. As a result, the operation safety of the endoscope 12 can be ensured.

Further, in the endoscope system 10, a plurality of semiconductor laser light sources LDs are used, and hence, by monitoring a drive current and a light quantity of each of the semiconductor laser light sources LDs, the drive current for an element larger in degradation ratio is decreased to suppress the degradation, and the drive current for an element smaller in degradation ratio is increased, thereby enabling the light quantity to be ensured.

The semiconductor laser light sources LD1 and LD2 may be light sources different in wavelength from each other. For example, it is preferred that one of the optical fibers 34 and 36 guide a light beam of 445 nm in wavelength, and the other guide a light beam of 405 nm in wavelength which is more excellent in the efficiency of phosphor excitation, to thereby improve the conversion efficiency of light. As a result, a calorific value of the phosphor converter 42 can be so suppressed as to obtain stable light emission. Besides, the wavelength of the excitation light and the physical properties of the phosphor converter 42 can be so selected as to obtain the illumination light having a color suitable for the purpose of observation with the endoscope 12.

In this case, when one of the optical fibers 34 and 36 is damaged, or when one of the semiconductor laser light sources LD1 and LD2 is suddenly degraded, though the light quantity and wavelength (color tone) of the illumination light are changed, the illumination light does not become zero. Accordingly, it is possible to ensure the operation safety of the endoscope 12.

Further, in the above-mentioned example, a part of the input light (excitation light) from the light sources is converted in wavelength by the phosphor converter 42. Alternatively, it is possible that the phosphor is selected to convert all of the input light in wavelength so as to obtain an output light having a desired color suitable for the observation. That is, in the above-mentioned example, as described above, the phosphor is excited by a blue light beam, a part of the blue light beam is converted into a yellow-green light beam and a red light beam, and the remaining blue light beam (light beam passing through the converter) is combined with the converted light beams to obtain a white color light beam. However, in order to enhance a color rendering property, it is desirable to excite phosphors of three colors RGB with a light beam in a violet to ultraviolet (400 nm or less, for example, 380 nm or 365 nm) region. When phosphors are further increased such that an orange color is added to RGB, an output light beam still higher in color rendering property can be obtained.

In the above-mentioned example, the two semiconductor laser light sources LD1 and LD2, and the two optical fibers 34 and 36 are used, the light sources and the optical fibers are connected one to one, and the light beams are guided from the light sources to the distal end portion 28 by the two optical fibers 34 and 36. However, other configurations can be applied as long as two or more optical fibers can be arranged in at least the angle portion 26. For example, light beams from three or more light sources can be guided up to the optical coupling circuit 38 by three or more optical fibers. Further, the number of light sources and the number of optical fibers may be identical with or different from each other. For example, it is possible that light beams from two light sources are branched and guided by three or more optical fibers, and coupled together by the optical coupling circuit 38. Alternatively, it is possible that light beams from four light sources are coupled together two by two before the endoscope 12, guided by two optical fibers, and then coupled into one light beam by the optical coupling circuit 38. Further, it is possible that the light beam is guided by one optical fiber in the part between the connector section 22 and the operation section 18, which is less frequently bent.

Subsequently, a second embodiment of the present invention is described.

Figure 3:
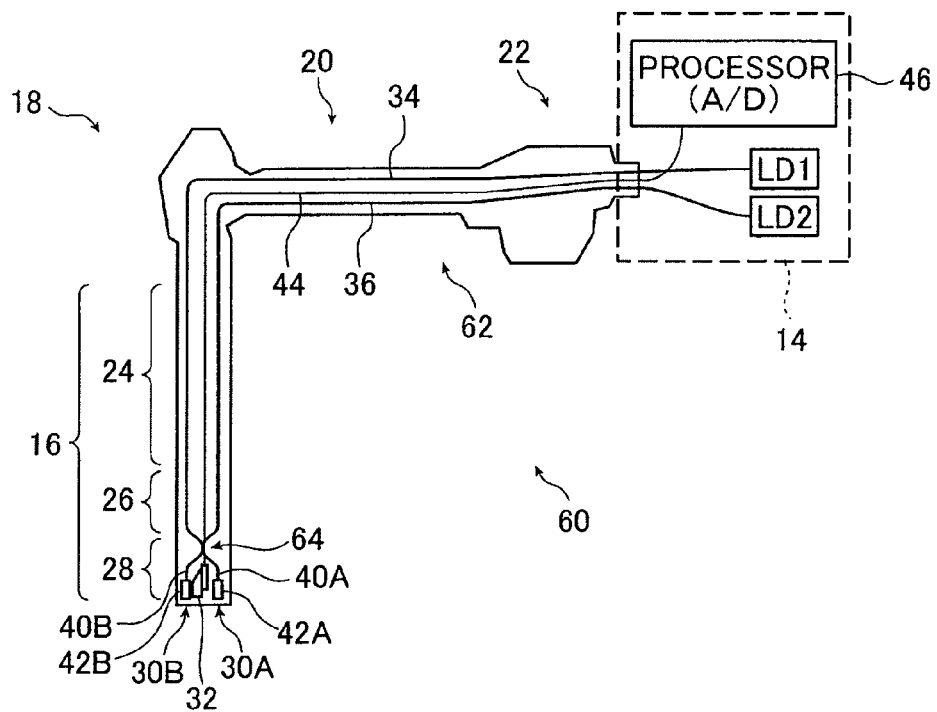
FIG. 3 is a schematic cross-sectional diagram illustrating a second embodiment of the present invention.

FIG. 3 is a schematic diagram illustrating a second example of an endoscope system using an endoscope lighting device according to the present invention. An endoscope system 60 illustrated in FIG. 3 emits illumination light beams from two points at the distal end of the endoscope 62.

In many of existing general endoscopes, illumination light beams are emitted from two points at the distal end of the endoscope in order to prevent an oversight due to illumination unevenness or shadow within the field of view. The endoscope system 60 provides such a two-lighting type endoscope light source device.

The endoscope system 60 is identical in configuration with the endoscope system 10 described above with reference to FIG. 1 except for the configuration of the distal end portion 28 of the endoscope 62. In FIG. 3, the same components as those of the endoscope system 10 of FIG. 1 are denoted by identical characters, and their detailed description is omitted.

An optical coupling/branching circuit 64 is disposed in the distal end portion 28 of the endoscope 62. The optical coupling/branching circuit 64 couples the optical fibers 34 and 36 into one optical fiber, and thereafter again branches the optical fiber into two optical fibers 40A and 40B. As the optical coupling/branching circuit 64, the combination of two Y-branching circuits each being identical with that of the optical coupling circuit 38 in the above-mentioned example, a bulk type optical circuit using a prism, an optical waveguide type optical-circuit such as a directional coupler, or a fiber fusion splicing type optical circuit can be used. It is preferable to use as the optical coupling/branching circuit 64 a circuit in which a coupling circuit and a branching circuit are integrated because the number of parts is small and assembling is simple. Alternatively, it is possible that the coupling circuit and the branching circuit are prepared separately, connected to each other, and arranged in the distal end portion 28.

In an end surface of the distal end portion 28 are disposed two illumination windows 30A and 30B, and phosphor converters 42A and 42B are arranged in the vicinity of the illumination windows 30A and 30B, respectively.

The laser beams from the two semiconductor laser light sources LD1 and LD2 are guided by the two optical fibers 34 and 36, and coupled into one laser beam by the optical coupling/branching circuit 64, and thereafter again branched into two laser beams. The branched laser beams have the same wavelength component (spectroscopic characteristic), and excite the phosphor converters 42A and 42B, respectively, to make them output illumination light beams through the two illumination windows 30A and 30B.

In the endoscope system 60 thus configured, even if one of the two optical fibers 34 and 36 is disconnected halfway, and also even if one of the two semiconductor laser light sources LD1 and LD2 stops light emission by reason of failure, the laser beam from a light source is guided up to the optical coupling/branching circuit 64 owing to the other laser light source or optical fiber, branched by the optical coupling/branching circuit 64, and input to both of the two phosphor converters 42A and 42B. As a result, the two phosphors in the endoscope distal end portion can emit light beams so as to emit the illumination light beams from the two illumination windows 30A and 30B. Accordingly, though it becomes darker within the field of view for imaging, any area in which it is particularly difficult to view, such as shadows, can be prevented from occurring, and when the insertion section 16 of the endoscope 62 is drawn out of the body, the insertion section 16 can be drawn out with safety and ease while checking a video.

It should be noted that, also in the endoscope system 60 illustrated in FIG. 3, the excitation light beams need only to be guided by two or more optical fibers in at least the angle portion 26. Alternatively, three or more optical fibers can be used, and three or more semiconductor laser light sources can be used.

In the endoscope system 60, the semiconductor laser light sources LD1 and LD2 may be different in wavelength from each other. The light beams from the respective semiconductor laser light sources LD1 and LD2 can be branched into two beams each having the same wavelength component after having been coupled together by the optical coupling/branching circuit 64, and the same illumination light can be obtained from the two illumination windows 30A and 30B by inputting the light beams having the same wavelength component to the phosphor converters 42A and 42B.

Next, a third embodiment of the present invention is described.

Figure 4:
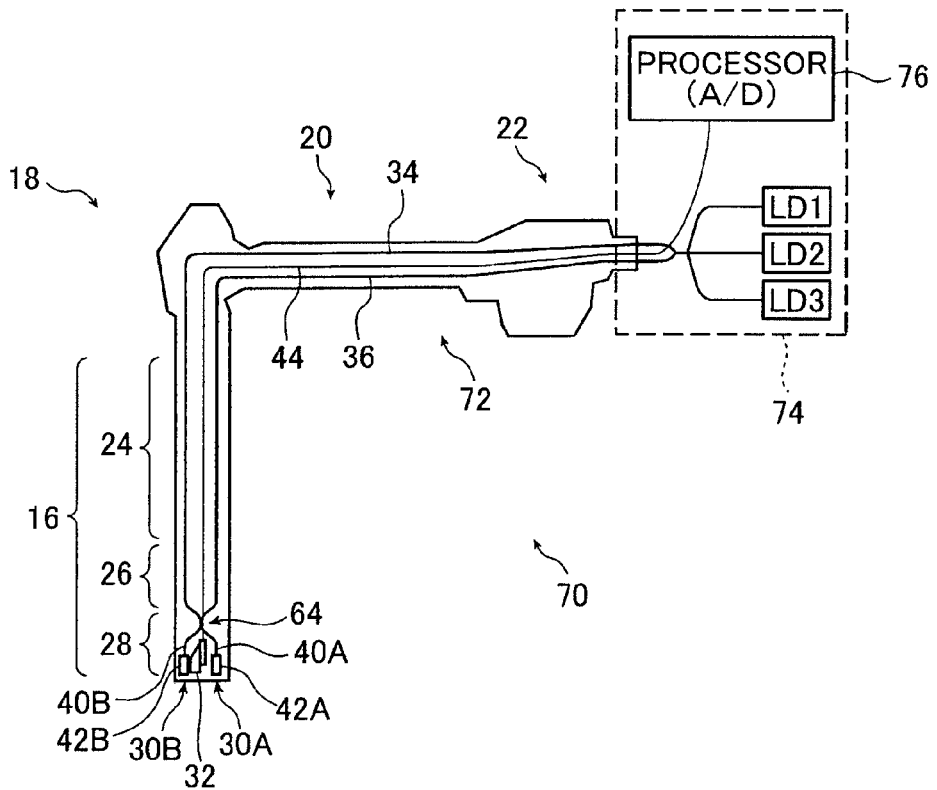
FIG. 4 is a schematic cross-sectional diagram illustrating a third embodiment of the present invention.

FIG. 4 is a schematic diagram illustrating a third example of an endoscope system using an endoscope lighting device according to the present invention. An endoscope system 70 illustrated in FIG. 4 includes an endoscope 72 and a control device 74. The endoscope 72 is of the same configuration as that of the endoscope 62 in the endoscope system 60 of FIG. 3, and emits two illumination light beams from the distal end. The control device 74 is different from the control device 14 in the endoscope system 60 of FIG. 3 in that three semiconductor laser light sources are provided.

When three or more semiconductor laser light sources LDs are provided, one optical fiber may be connected to each of the light sources so as to cause the optical fibers to guide light up to the distal end portion of the endoscope 72. However, the optical coupling/branching circuit 64 becomes larger in size as the number of optical fibers increases. In addition, the cross-sectional area of the endoscope 72 occupied by the optical fibers located therein is increased. For that reason, when three or more semiconductor laser light sources LDs are provided, it is preferred that the optical fibers connected to the semiconductor laser light sources LDs be coupled together, then branched into two, before the endoscope 72, and subsequently inserted into the endoscope 72, as in the endoscope system 70 illustrated in FIG. 4.

Similarly in the endoscope system 70, even if one of the two optical fibers 34 and 36 is disconnected halfway, though the quantity of illumination light is reduced, the two phosphor converters 42A and 42B disposed in the endoscope distal end portion can be made to emit light so as to emit illumination light beams from the two illumination windows 30A and 30B. Further, even when one of the three semiconductor laser light sources LD1, LD2, and LD3 stops light emission, at least half the normal light quantity can be ensured, and even when two of the light sources stop light emission, the field of view does not become pitch-dark.

In the examples of FIGS. 3 and 4, the configuration of the lighting device in the distal end portion 28 of each of the endoscopes 62 and 72 may be such that the optical coupling/branching circuit 64 is branched into three or more on its branching side, and a corresponding number of the phosphor converters and illumination windows are disposed, that is to say, three or more illumination light beams are provided at the endoscope distal end.

In the above-mentioned respective examples, two or more semiconductor laser light sources LDs are used. When the lifetime of the laser light source LD can be ensured during use of the endoscope, or when the laser light source LD can be immediately replaced with another one if it stops, the configuration can be such that a single semiconductor laser light source LD is used. In this case, it is possible that the light beam from the semiconductor laser light source LD is branched into two light beams before the endoscope, and the two optical fibers 34 and 36 are arranged in at least the angle portion 26 of the endoscope. A reduction in the number of semiconductor laser light sources LDs enables the costs to be suppressed.

Examples in each of which a single semiconductor laser light source LD is used are described as a fourth embodiment and a fifth embodiment of the present invention.

Figure 5:
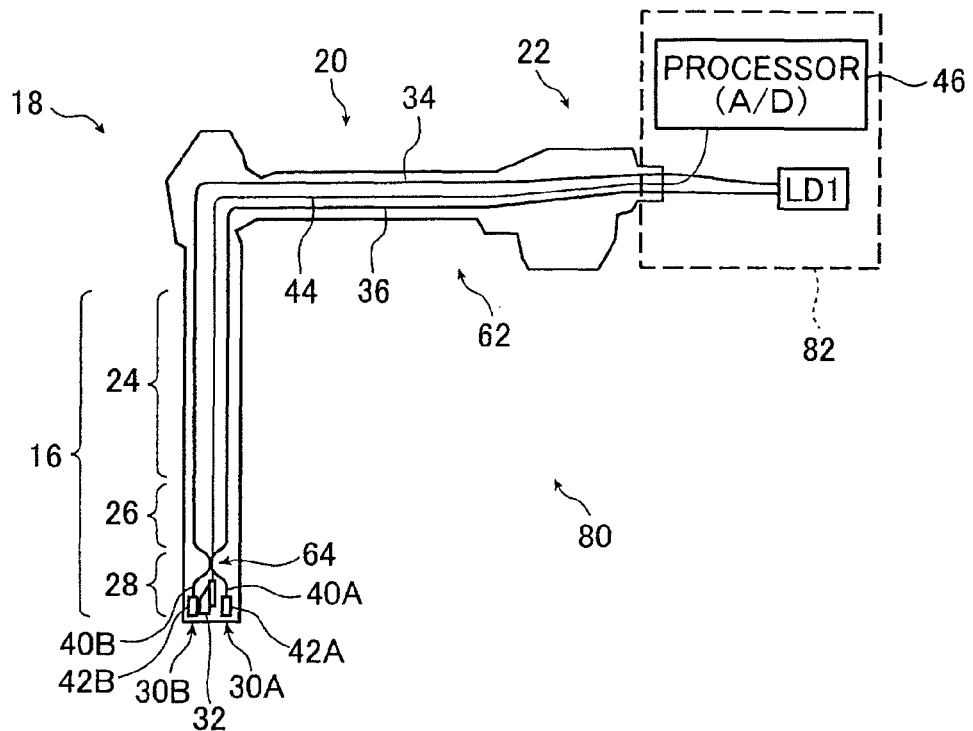
FIG. 5 is a schematic cross-sectional diagram illustrating a fourth embodiment of the present invention.

FIG. 5 is a schematic diagram illustrating a fourth example of an endoscope system using an endoscope lighting device according to the present invention. An endoscope system 80 illustrated in FIG. 5 includes an endoscope 62 having two illumination light beams emitted from the distal end as in the case of the endoscope 62 of the second embodiment illustrated in FIG. 3, and a control device 82 having one semiconductor laser light source LD1 and a processor 46.

In this embodiment, as the semiconductor laser light source LD1, there is used a multi-transverse mode laser light source called "broad area laser". The light emission width of the semiconductor laser light source LD1 is, for example, 50 to 100 μm. A laser beam from the semiconductor laser light source LD1 is narrowed down to provide a slender laser beam, and the ends of the optical fibers 34 and 36 are arranged close to each other in the longitudinal direction of the laser beam, thereby making it possible to feed the light beam from one semiconductor laser light source LD1 into the two optical fibers 34 and 36 at the same time.

The laser beam fed from the semiconductor laser light source LD1 into the optical fibers 34 and 36 is guided by each of the optical fibers 34 and 36, and after the laser beams thus guided are coupled into one laser beam by the optical coupling/branching circuit 64, the laser beam is again branched into two laser beams, as in the above-mentioned example of FIG. 3. The branched laser beams have the same wavelength component (spectroscopic characteristic), and excite the phosphor converters 42A and 42B, respectively, to make them output illumination light beams through the two illumination windows 30A and 30B.

The configuration of the lighting device in the distal end portion 28 of the endoscope 62 may be such that, apart from the application of two illumination light beams, one illumination light is applied as in the endoscope 12 of the endoscope system 10 illustrated in FIG. 1, or the optical coupling/branching circuit 64 is branched into three or more on its branching side, and a corresponding number of phosphor converters and illumination windows are disposed, so as to provide three or more illumination light beams at the endoscope distal end. Further, it is possible that the laser beam from the semiconductor laser light source LD1 is fed into three or more optical fibers at the same time, and guided within the endoscope 62 by the three or more optical fibers.

Figure 6:
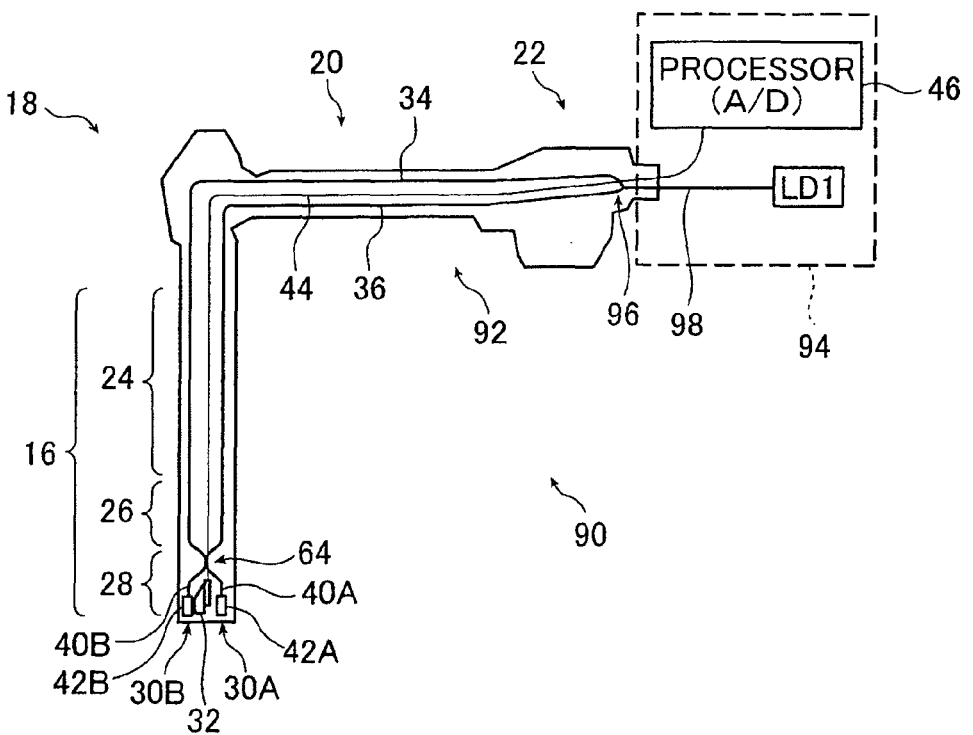
FIG. 6 is a schematic cross-sectional diagram illustrating a fifth embodiment of the present invention.
Figure 7:
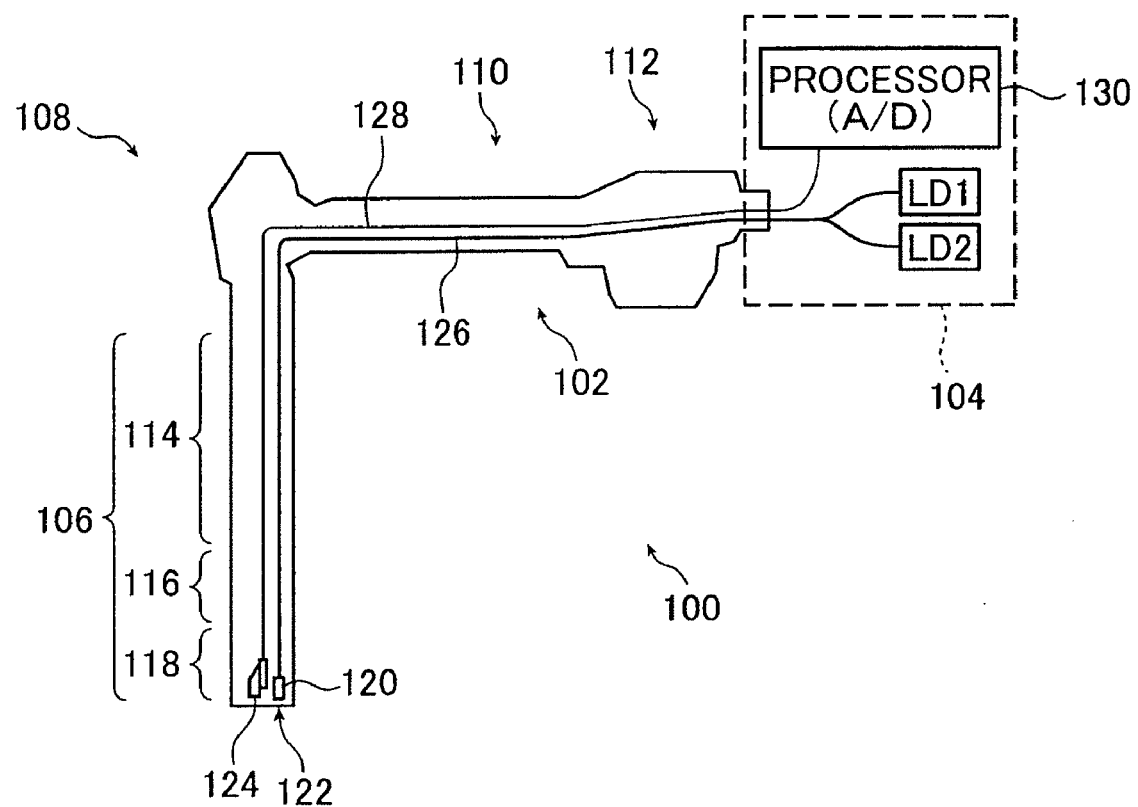
FIG. 7 is a schematic cross-sectional diagram illustrating an example of a conventional endoscope device.

FIG. 6 is a schematic diagram illustrating a fifth example of an endoscope system using an endoscope lighting device according to the present invention. An endoscope system 90 illustrated in FIG. 6 includes an endoscope 92 having two illumination light beams emitted from the distal end, and a control device 94 having one semiconductor laser light source LD1 and a processor 46.

The endoscope 92 has an optical branching circuit 96 in the connector section 22. The optical branching circuit 96 connects one optical fiber 98 that extends outside the endoscope 92 and is connected to the semiconductor laser light source LD1 with the two optical fibers 34 and 36 to branch a light beam transmitted from the semiconductor laser light source LD1 by the optical fiber 98 into two light beams. It is important that the optical branching circuit 96 is arranged on the proximal end side (connector side) with respect to the angle portion 26. Preferably, the optical branching circuit 96 is arranged in the connector section 22 which is less frequently bent and close to the proximal end. Alternatively, it is possible that the optical branching circuit 96 is disposed in the control device 94, and each of the two optical fibers 34 and 36 that extend from the endoscope 92 is connected to the optical branching circuit 96 disposed within the control device 94.

The configuration of the endoscope 92 other than the above-mentioned is identical with that of the endoscope 62 of FIG. 5, and the configuration of the lighting device in the distal end portion 28 of the endoscope 92 can be such that one illumination light, or three or more illumination light beams are used, apart from the use of two illumination light beams, as in the endoscope 62 of FIG. 5. Further, it is possible that the light beam from the semiconductor laser light source LD1 is branched into three or more light beams in the light branching circuit 96, and those light beams are guided within the endoscope 92 by three or more optical fibers.

The above description has been given in detail of the endoscope light source device according to the present invention.

However, the present invention is not limited to the above-mentioned embodiments, and it is obvious that various improvements and changes may be made without departing from the scope of the present invention.

What is claimed is:

1. An endoscope light source device comprising:
at least one semiconductor light source;
first optical fibers that have a single core, are inserted into a bendable endoscope, guide first light beams from said at least one semiconductor light source, and are arranged in plural rows in at least an angle portion of an insertion portion of said endoscope;
an optical coupling circuit that is arranged at a distal end side of said endoscope with respect to said angle portion, and that couples said first light beams guided by said first optical fibers arranged in the plural rows to obtain a coupled light beam;
at least one second optical fiber that guides said coupled light beam coupled by and outputted from said optical coupling circuit; and
at least one wavelength conversion part that is arranged at a distal end side of an endoscope insertion section in said optical coupling circuit, and converts a part or all of said coupled light beam coupled by said optical coupling circuit and guided by said at least one second optical fiber into a converted light beam having a given wavelength by a phosphor.

2. The endoscope light source device according to claim 1, wherein plural second optical fibers are provided, and said endoscope light source device further comprises:
an optical branching circuit that is disposed at said distal end side of said endoscope insertion section in said optical coupling circuit, and branches said coupled light beam from said optical coupling circuit into second light beams to output said second light beams to said plural second optical fibers, respectively,
wherein said at least one wavelength conversion part includes plural wavelength conversion parts that are provided corresponding to said second light beams branched by said optical branching circuit and guided by said plural second optical fibers, respectively.

3. The endoscope light source device according to claim 2, wherein said optical coupling circuit and said optical branching circuit are integrated with each other.

4. The endoscope light source device according to claim 2, wherein a pair of wavelength conversion parts, a window, an imaging element for acquiring image information on an observed region illuminated with the converted light beam having the given wavelength that is converted by said pair of wavelength conversion parts, and an objective lens are disposed at said distal end side of said endoscope insertion section, and
said imaging element is disposed between the wavelength conversion parts of said pair.

5. The endoscope light source device according to claim 1, wherein said at least one semiconductor light source includes plural semiconductor light sources that are provided outside of said endoscope, and
said optical fibers arranged in the plural rows are respectively connected to said plural semiconductor light sources different from each other.

6. The endoscope light source device according to claim 5, wherein said plural semiconductor light sources includes at least two semiconductor light sources for emitting the first light beam in wavelength different from each other.

7. The endoscope light source device according to claim 5, further comprising:

a second optical branching circuit that branches one light beam from one or more semiconductor light sources into branched light beams to output said branched light beams to said first optical fibers.

8. The endoscope light source device according to claim 7, wherein said at least one semiconductor light source includes one semiconductor light source that is disposed outside of said endoscope, and said endoscope light source device further comprises:

a third optical fiber that guides a light beam from said one semiconductor light source; and a light source side optical branching circuit that divides the light beam emitted from said one semiconductor light source and guided by said third optical fiber into plural light beams and that is disposed between said one semiconductor light source and said endoscope, or disposed on a proximal end side with respect to said angle portion within said endoscope.

9. The endoscope light source device according to claim 1, wherein said at least one semiconductor light source includes one semiconductor light source that is disposed outside of said endoscope, and said optical fibers arranged in the plural rows are connected to said one semiconductor light source.

10. The endoscope light source device according to claim 1, wherein said optical coupling circuit is arranged at a distal end side of said endoscope with respect to said angle portion.

* * * * *